US010357167B2

(12) United States Patent
Hernandez-Silveira et al.

(10) Patent No.: US 10,357,167 B2
(45) Date of Patent: Jul. 23, 2019

(54) METHOD FOR CONFIDENCE LEVEL DETERMINATION OF AMBULATORY HR ALGORITHM BASED ON A THREE-WAY RHYTHM CLASSIFIER

(71) Applicant: SENSIUM HEALTHCARE LIMITED, Oxfordshire (GB)

(72) Inventors: Miguel Hernandez-Silveira, Oxfordshire (GB); Su-Shin Ang, Oxfordshire (GB)

(73) Assignee: SENSIUM HEALTHCARE LIMITED, Abingdon (GB)

( * ) Notice: Subject to any disclaimer, the term of this patent is extended or adjusted under 35 U.S.C. 154(b) by 171 days.

(21) Appl. No.: 14/710,943

(22) Filed: May 13, 2015

(65) Prior Publication Data
US 2015/0327781 A1 Nov. 19, 2015

(30) Foreign Application Priority Data

May 13, 2014 (GB) .................................. 1408485.9

(51) Int. Cl.
*A61B 5/0245* (2006.01)
*A61B 5/00* (2006.01)
*A61B 5/0452* (2006.01)

(52) U.S. Cl.
CPC .......... *A61B 5/0245* (2013.01); *A61B 5/0452* (2013.01); *A61B 5/7221* (2013.01); *A61B 5/7264* (2013.01); *A61B 5/7203* (2013.01)

(58) Field of Classification Search
CPC . A61L 35/7203; A61B 5/0245; A61B 5/7221; A61B 5/0452; A61B 5/7264; A61B 5/7203
See application file for complete search history.

(56) References Cited

U.S. PATENT DOCUMENTS 8,315,699 B2 11/2012 Stadler et al.
8,521,268 B2 8/2013 Zhang et al.
(Continued)

FOREIGN PATENT DOCUMENTS

EP 2 389 858 A2 11/2011
EP 2 468 180 A2 6/2012
(Continued)

OTHER PUBLICATIONS

Li et al., Physiological Measurement, Institute of Physics Publishing, vol. 29, No. 1, pp. 15-32 (Jan. 1, 2008) XP020130214.
(Continued)

*Primary Examiner* — Mark Bockelman
(74) *Attorney, Agent, or Firm* — Saul Ewing Arnstein & Lehr LLP (57) ABSTRACT

A method of determining a confidence level in a heart rate obtained from an ECG signal of a patent comprises determining a heart rate from a segment of an ECG signal, the segment having a pre-determined length, and determining a first confidence level in the determined heart rate. If the first confidence level exceeds a predetermined value, the heart rate is output. Otherwise, the method further comprises determining a set of features from the segment of the ECG signal; and classifying the segment of the ECG signal, based on one or more features selected from the determined set of features and the heart rate, into one of at least three classes: noise, an abnormal sinus rhythm and a normal sinus rhythm.

16 Claims, 5 Drawing Sheets

(56) References Cited

U.S. PATENT DOCUMENTS

| | | |
|---|---|---|
| 8,521,277 B2 | 8/2013 | Farazi et al. |
| 8,521,281 B2 | 8/2013 | Patel et al. |
| 2008/0214949 A1 | 9/2008 | Stovoric et al. |
| 2011/0270110 A1 | 11/2011 | Zhang et al. |
| 2013/0289424 A1 | 10/2013 | Brockway et al. |
| 2014/0005988 A1 | 1/2014 | Brockway |

FOREIGN PATENT DOCUMENTS

| | | |
|---|---|---|
| WO | 2007/036748 A2 | 4/2007 |
| WO | 2008/135985 A1 | 5/2008 |

OTHER PUBLICATIONS

Extended European Search Report, dated Sep. 29, 2015, issued in corresponding EP Application No. 15 167 186.4.
Combined Search and Examination Report, dated Oct. 27, 2014, issued in priority UK Application No. GB1408485.9.

METHOD FOR CONFIDENCE LEVEL DETERMINATION OF AMBULATORY HR ALGORITHM BASED ON A THREE-WAY RHYTHM CLASSIFIER

CROSS-REFERENCE TO RELATED APPLICATIONS

This application is based on, and claims priority to, UK Application No. 1408485.9, filed May 13, 2014, the entire contents of which is fully incorporated herein by reference.

FIELD OF THE INVENTION

The present invention relates to a method for determining a confidence level in a heart rate obtained from a patent, for example from an ECG signal of the patent.

BACKGROUND OF THE INVENTION

According to findings by the National Institute for Healthcare and Clinical Excellence (NICE), there is evidence that patients are receiving sub-optimal care in hospitals because indications of clinical deterioration were not appreciated or not acted upon in time. Vital signs are typically recorded by nurses three times a day, that is every 8 hours. There is a large body of evidence indicating that during these intervals one or more adverse physiological events flagging patient deterioration are likely to occur.

Different clinicians have expressed the need for monitoring patients continuously, so that the appropriate level of response can be quickly administered to prevent patient deterioration following early warning signs. This has motivated different research and development of monitoring systems that are effective in reducing mortality rates and improving patient outcomes in clinical studies conducted around the world.

In response to this need, Toumaz Healthcare Ltd has developed a patient surveillance system around ultra-low power wireless wearable technologies, as described in EP 1928311 and US 2008-0214946, the contents of which are hereby incorporated by reference. Patients in general wards are patched up with a low cost, light-weight and unobtrusive wireless digital plaster that continuously monitors heart rate (HR), respiration activity and temperature. Thereby, physiological data from patients are transmitted via hotspots (bridges) to one or more servers that enable further analysis and presentation of the values and trends of vital signs in computer monitors. Such central stations are programmed to generate notifications/alerts when the nominal values of one or more of these parameters have exceeded preset limits. Thus, the medical staff is warned about adverse physiological events which may lead to posterior deterioration of the patient if left untreated.

Figure 2:
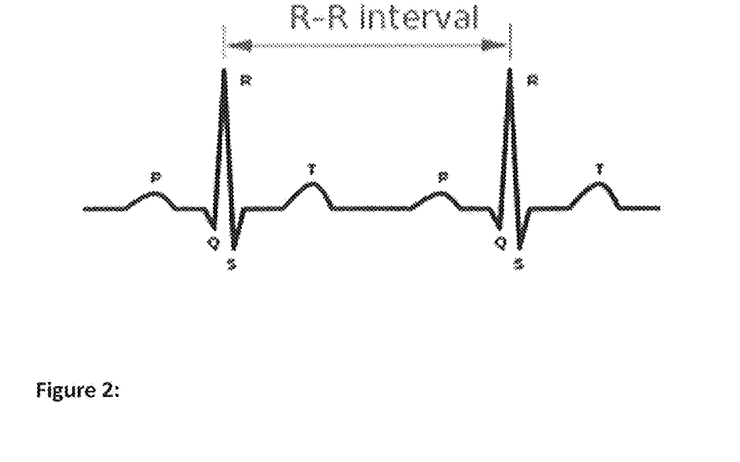
FIG. 2 show a typical heartbeat.

FIG. 2 is a schematic illustration of a portion of a typical ECG for a healthy patient. The heart rate (typically measured in beats per minute) is determined from the time between adjacent R peaks in the ECG signal. Systems that can determine the HR from an ECG signal are known—for example they may use "QRS detection" to identify occurrences of the three peaks labelled "Q", "R" and "S" in FIG. 2. For example, QRS detection and determination of the HR may be performed according to the Open Source ECG Analysis (OSEA) model, P. S. Hamilton, 'Open Source ECG Analysis Software (OSEA) Documentation', www.eplimited.com.

The majority of patients in a general ward are ambulatory in nature. This introduces an additional challenge to early warning monitoring technologies. Motion of a patent often results in artifacts contaminating the physiological signals (such as the ECG) obtained from that patient, owing to electrical signals generated by movement of the patient's muscles. Such noise in a physiological signal not only affects the quality and/or reliability of the processed physiological values, but often increases the incidence of false alerts. Accredited reports have pointed out that a high incidence of false alerts is dangerous as it might lead to the desensitization of the clinical staff to adverse physiological events; and hence, failure to trigger the timely response of the adequate medical teams to patient deterioration—see, for example, Emergency Care Research Institute, "Health Devices—Top 10 Health Technology Hazards for 2013", 2013.

Unfortunately, the issue of artifacts in physiological signals arising from motion of the patient is complex, since such type of noise is always larger in amplitude and is in-band with the physiological phenomena being measured. This situation is aggravated in the case of low-cost wireless single-lead ECG monitoring technologies, where the absence of additional reference signals from alternative sensors and lack of computational power makes difficult and often impossible to cancel the noise and recover the meaningful information from the physiological data—see, for example S. Choi, and Z. Jiang, "A wearable cardiorespiratory sensor system for analyzing sleep condition", in Journal of Expert systems with applications; 2008, A. Johansson, "Neural network for photoplethysmorgraphic respiratory rate monitoring", in Journal of Medical and Biological Engineering and Computing, 2003; or K. Nuzeki, et. al., "Unconstrained cardiorespiratory and body movement monitoring system for home care", in Proceedings of the International Conference on Acoustics, Speech, and Signal Processing, 2005.

Motion artifacts and other forms of noise exhibit a non-periodic and stochastic (non-deterministic) behavior. This characteristic has been exploited by developers of single-lead ambulatory monitors, in order to discard invalid readings that stem from severely corrupted data—see M. A. Hernandez-Silveira, S. Ang, and A. Burdett, "Wearable Ambulatory Sensor Devices: Challenges and Trade-offs in the Development of Embedded Algorithms for Vital Signs Monitoring", in the Proceedings of International Conference on Biomedical Engineering, 2013. Typically, the approach involves multivariate statistical estimation and quantification of the regularity and stationarity of the signals to determine the level of confidence in the interpretation or processed value. That is, ECG signals from a patient may be processed to determine both a heart rate and a confidence value associated with the determined heart rate. For example, in the case of single-lead ECG obtained from an ambulatory patient, an error code can be displayed when the confidence level in the determined HR is low (i.e. when the ECG is severely corrupted by noise arising from the patient's movement), instead of presenting the computed heart rate value that would be displayed on the screen if the results of the confidence estimation were high (as would be the case for a heart rate determined from a good quality, low-noise ECG). Unless the number of error codes exceeds a preset threshold (set by the clinical staff), a notification will not be triggered. For healthy individuals with no history of cardiac arrhythmias, we believe that this approach would be effective in its prediction and it would lead to reduction of false alerts.

Unfortunately, this approach is not suitable for patients with certain cardiac abnormal rhythms, such as atrial fibrillation (AF). Atrial fibrillation shows as an aperiodic rhythm in a patient's heartbeat, characterized by irregular inter-beat intervals and rapid ventricular contractions. (In a patient suffering from AF the P-waves shown in FIG. 2 are not present, leading to an abnormal heart rhythm.) It is desirable that a high HR in a patient who suffers from AF would trigger a notification or alert when detected by the monitoring system. Regrettably, however, the opposite would actually occur in a system merely based in the confidence indication approach described above—i.e. the system would deem this abnormal rhythm as noise and assign a low confidence level to the determined HR—and consequently the system would generate error codes, rather than presenting the actual high HR value and triggering the required alert.

Solving this problem is advantageous because AF is very common in the general ward, and is usually first-time diagnosed in a large proportion of the patients during their stay. Furthermore, the number of people who will be suffering from this type of arrhythmia is expected to rise substantially in the next 50 years (M. Cvach, "Monitor Alarm Fatigue: an Integrative Review", in Journal of Biomedical Instrumentation and Technology, 2012). In addition, this arrhythmia usually leads to fatal conditions if left untreated—i.e. AF is usually associated with the onset of stroke and/or cardiac arrest.

Unfortunately, it is impractical and expensive to fit all patients in the general ward with traditional bedside devices. Instead, a far more attractive solution would be to improve low-cost wireless surveillance systems, to enable them to adequately process the abnormal HR value resulting from an aperiodic heart rhythm such as AF and trigger a notification/alert during its onset.

Many methods for automatic arrhythmia detection exist. These methods are currently incorporated in clinical bedside monitors and portable telemetry and Holter systems, as well as Implantable Medical Devices (IMD) such as pacemakers, for the purpose of arrhythmia detection. Also, in order for accurate diagnosis to take place, multi-lead ECG systems are often required. Some of these techniques are shown below.

U.S. Pat. No. 8,315,699 (Nov. 20, 2012): This method detects and discriminates between supraventricular tachycardia (SVT) from ventricular tachycardia (VT). This involves tracking increases in variability in the heart rate intervals when there is the variability in the RR intervals is low, and vice-versa.

U.S. Pat. No. 8,521,281 (Aug. 27, 2013): The proposed method comprises an implantable medical device that determines the existence of Atrial Fibrillation (AF) based on whether one atrial interval is greater/lesser than pre-determined thresholds, the amplitude of an atrial sensed event is lesser than another pre-determined threshold, and if the intervals from the Ventricular sensed events are irregular.

U.S. Pat. No. 8,521,277 (Aug. 27, 2013): The proposed method comprises an implantable medical device that detects Atrial Fibrillation by provoking an atrial evoked response. The patient is deemed to be suffering from AF if a change in one of the atrial evoked response metrics occurs over time. These metrics include the minimum/maximum amplitude of the response, peak-to-peak interval, as well as duration, area, slope, and timing of the response.

U.S. Pat. No. 8,521,268 (Aug. 27, 2013): The proposed method makes use of a template, encompassing the first two peaks in the signal, and comparing this template with other pairs of peaks within the signal. AF is detected based on the similarities between the template and the signal.

As yet, there is no evidence in the current state of the art reporting or suggesting the use of methods to enhance the reliability of single-lead HR algorithms intended for ambulatory monitoring purposes only.

SUMMARY OF THE INVENTION

A first aspect of the present invention provides a method comprising: determining a heart rate from a segment of an ECG signal, the segment having a pre-determined length, and determining a first confidence level in the determined heart rate; if the first confidence level exceeds a predetermined value, outputting the heart rate; otherwise: determining a set of features from the segment of the ECG signal; and classifying the segment of the ECG signal based on one or more features selected from the determined set of features and the heart rate; wherein classifying the segment of ECG signal comprises classifying the segment of ECG signal as any one of at least three classes: noise, an abnormal sinus rhythm and a normal sinus rhythm.

The present invention proposes enhancing the confidence estimator, so that it may discriminate between a normal rhythm, an abnormal rhythm and noise (whereas conventional algorithms can only discriminate between noise and a normal rhythm). In simple terms, instead of aiming to use sophisticated and burdensome and expensive arrhythmia detection systems for diagnosis, the invention enables an affordable single-lead wireless monitoring system with the ability of displaying abnormal HRs in the presence of abnormal rhythms. This will allow the nursing staff responsible for the hospitalization floor to request the intervention of the appropriate specialist when suspecting on the existence of this arrhythmia and prescribe adequate diagnosis tests. The invention thus makes possible an improved low-cost wireless surveillance systems, that may adequately process the abnormal HR value resulting from an aperiodic heart rhythm such as AF and trigger a notification/alert during its onset.

The invention may classify a segment of ECG signal into exactly the three classes of noise, an abnormal sinus rhythm and a normal sinus rhythm. It should however be understood that the invention is not limited to classifying a segment of ECG signal into any one of only three classes, and the invention may optionally be able to classify a segment of ECG signal into any one of four, or even more, classes. For example, the invention may optionally be able to discriminate between two different abnormal sinus rhythms, and so be able to classify a segment of ECG signal as any one of: noise, a first abnormal sinus rhythm, a second abnormal sinus rhythm (different to the first abnormal sinus rhythm) and a normal sinus rhythm.

We propose a novel approach that combines a three-way (or higher) classification method with the existing capabilities of the decision making stage of an algorithm for determining the heart rate, so that valid heart rate values may be displayed and further processed only if they correspond to normal or abnormal (periodic and aperiodic) rhythms. In principle the three-way (or higher) classifier will be able to discriminate between noise signals from normal rhythms and noise signals from aperiodic rhythms (AF and others such as heart blocks, extrasystoles, etc.). It should be borne in mind that the use of this classifier is not for diagnosis purposes. In contrast, it is merely for improving monitoring capabilities ECG systems, such as low cost single-lead ECG systems—i.e. adding more confidence in the processed HR values and allowing more reliable identification of abnormal rhythms and thus decreasing the net amount of HRs that are ignored due to the aperiodic nature of certain abnormal rhythms.

An embodiment of the invention is the use of arrhythmia detection techniques in combination with statistical and heuristic rules to enhance the robustness and reliability of HR monitoring algorithms by rejecting those signals severely corrupted by noise, and allowing calculations of reliable HRs whether they stem from normal heart rhythms or from abnormal (aperiodic) heart rhythms.

The present invention processes data in segments of a pre-determined length. From each segment, a resulting class is computed, and the class may either be noise, abnormal sinus rhythm (such as Atrial Fibrillation), or Normal Sinus Rhythm. To the best of our knowledge, there are no classifiers reported in prior art that discriminates noise separately from abnormal and normal rhythms.

The module for computing the class of a segment may be incorporated as an extension to an existing HR algorithm, rather than being merged in the code. This provides advantages. First, this enhances the performance of an HR existing algorithm without changing its internal logic and structure. Second, its addition as a subsequent stage makes it easier to disable/enable different sub-modules within the algorithm. Third, it makes it easier to maintain the code.

The method may comprise, if classifying the segment of the ECG signal comprises classifying the segment of the ECG signal as indicative of an abnormal sinus rhythm or indicative of a normal sinus rhythm, outputting the determined heart rate after classifying the segment of the ECG signal.

The method may comprise, if classifying the segment of the ECG signal comprises classifying the segment of the ECG signal as indicative of noise, further comprising outputting an error indication.

Determining the first confidence level may comprise comprises determining a noise level in the segment of the ECG signal.

Determining the set of features may comprise processing the segment and determining the set of features from the processed segment.

Classifying the segment of the ECG signal may comprise classifying the segment of the ECG signal based on two features selected from the determined set of features and the heart rate.

The ECG signal may be a single lead ECG signal.

A second aspect of the invention provides an apparatus comprising: a module configured to determine a heart rate from a segment of an ECG signal, the segment having a pre-determined length, and to determine a first confidence level in the determined heart rate; a module configured to, if the first confidence level exceeds a predetermined value, output the heart rate; a module configured to, if the first confidence level does not exceed the predetermined value, determine a set of features from the segment of the ECG signal; and a classifying module configured to classify the segment of the ECG signal based on one or more features selected from the determined set of features and the heart rate; wherein the classifying module is configured to classify the heart rate determined from the segment of ECG signal into any one of at least three classes: noise, an abnormal sinus rhythm and a normal sinus rhythm.

The apparatus may be configured to, if the classifying module classifies the segment of the ECG signal as an abnormal sinus rhythm or a normal sinus rhythm, output the determined heart rate.

The apparatus may be configured to classify the segment of the ECG signal based on two features selected from the determined set of features and the heart rate.

The apparatus may further comprise an input for receiving an ECG signal.

The apparatus may comprise a segmenter module configured to segment an ECG signal received at the input.

A third aspect of the invention provides a system comprising an apparatus of the second aspect and a single lead ECG system connectable to the input of the apparatus.

A fourth aspect of the invention provides a non-transitory computer-readable medium containing instructions that, when executed on a processor, cause the processor to carry out a method of the first aspect.

DETAILED DESCRIPTION

Figure 1:
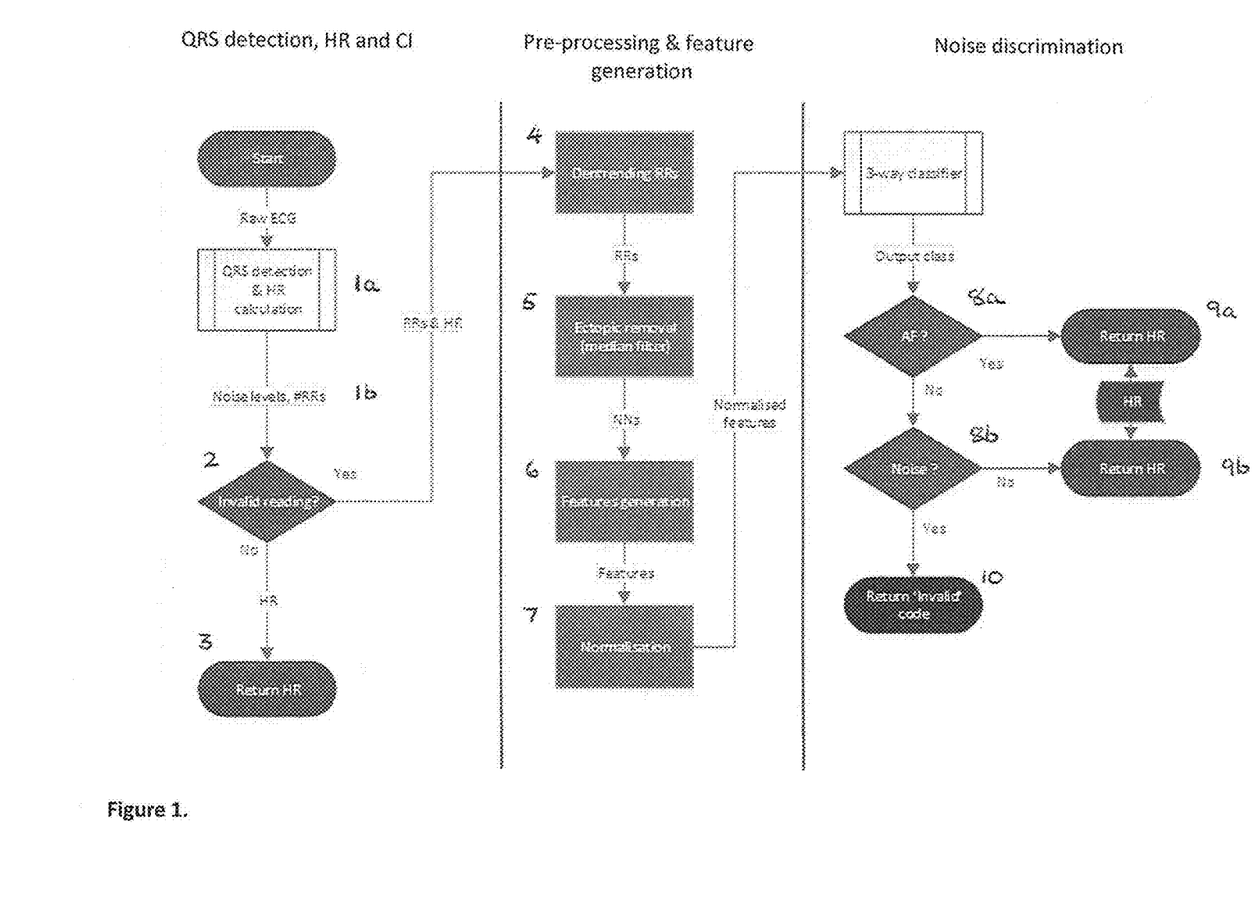
FIG. 1 illustrates principal features of a method according to the present invention.

FIG. 1 shows principal features of a method according to one embodiment of the present invention, which incorporates arrhythmia and noise detection techniques in determining the level of confidence in the calculated heart rate. More specifically, there are two stages in determining the level of confidence of the HR. The application of the second stage allows a larger proportion of heart rates to be recovered if the ECG segment is re-classified as AF or Normal, after having been classified as invalid in the first stage of determining the confidence level in the heart rate. Potentially, this will allow a notification to be triggered early if the recovered heart rates are out of the normal physiological range.

The principal stages of the method of FIG. 1 are as follows:

1. The patient's heart rate HR (eg the RR interval shown in FIG. 2) is determined (1a) for a segment of the patient's ECG signal. The RR intervals may be extracted from the ECG segment using any suitable technique, for example by using a peak detector to identify the R peaks in the ECG segment, or a QRS detection and HR calculation module may be applied to an ECG segment of a pre-determined length at stage 1 to determine the patient's heart rate. Any suitable QRS detection method may be used, for example a method that implements the OSEA model. The segment of the ECG signal is typically of a pre-determined length, and is of a length that is equal to several times the RR interval so that a set of multiple RR intervals is obtained from the segment. The ECG signal may be obtained using a single-lead ECG monitoring technique, although the invention is not limited to use with single-lead ECG techniques.

This first stage also comprises a determination (1b) of the level of noise within the ECG signal and further comprises a determination, based on the determined noise level, of a first confidence level in the heart rate that is obtained from the ECG signals (eg a confidence level in the set of ECG peak-to-peak (RR intervals) intervals that is obtained). The outputs from this stage, for the segment of the ECG signal, thus may include a heart rate HR, as well as a measure of the noise in the segment of the ECG signal and an initial level of confidence in the HR determined from the segment of the ECG signal.

2. Next, at stage 2 a determination is made whether the heart rate obtained in the first stage is valid or invalid. This may for example be made by comparing the first level of confidence obtained in the first stage with a threshold level, and determining the heart rate obtained in the first stage to be valid if the level of confidence obtained in the first stage exceeds the threshold, otherwise determining the heart rate obtained in the first stage to be invalid.

3. If the heart rate obtained in the first stage is deemed to be valid, the heart rate determined for the segment is returned at stage 3 of FIG. 1.

Steps 1, 2 and 3 are typically repeated for many segments of the patient's ECG signal.

If however the heart rate obtained in the first stage is deemed at stage 3 to be invalid based the first confidence level calculation, a second confidence level calculation is applied. The second confidence level calculation comprises 2 stages:—pre-processing, and noise discrimination. The principal stages of the second confidence level calculation are as follows.

4. At stage 4, the set of RR intervals obtained from a segment of the ECG signal using the QRS detection algorithm is de-trended.

5. At stage 5, an ectopic filter is applied to the detrended RR intervals obtained from the previous stage, to remove outliers caused by spurious non-physiological spikes within the original signal. A resulting set of Normal RR intervals ("NNs") is obtained for the segment of the ECG signal.

6. At stage 6, a set of one or more relevant features is computed from the NNs that were produced for the segment of the ECG signal in the previous stage. These one or more features measure the degree of variability within the input set of NNs. The features include but are not restricted to the Root Mean Square of Successive Differences (RMSSD), Standard Deviation of Successive Differences (SDSD), Sample Entropy, Shannon Entropy, Turning-point ratio, Average Absolute Deviation, mean of the NN intervals, and the Standard Deviation of the NN intervals (SDNN). As noted each of these further features measures the degree of variability within the input set of NNs, so that an input set of NNs for a segment of the ECG signal is characterized by a single RMSSD value, by a single mean NN value, etc. The set of NNs obtained for the segment of the ECG signal is also characterised by the HR obtained for that segment at stage 1a; this HR value may be transmitted together with the segment through the process or may be stored after it has been obtained at stage 1a and retrieved as necessary.

7. At stage 7 the feature(s) obtained in step 6 for the segment of the ECG signal, and the heart rate, are then normalized. In a preferred embodiment one of three types of normalization techniques can be applied to the feature set. The first type is RMSSD normalization (normalize using the mean of the NN intervals), the second is Gaussian normalization (as shown in equation (1)), and the third is Range normalization (as shown in equation (2)).

$$GaussianNorm(f) = \frac{f - \overline{F}}{s^2} \quad (1)$$

$\overline{F}$: Mean feature value
$s$: Standard deviation of feature $$RangeNorm(f) = \frac{f - F_{min}}{F_{max} - F_{min}} \quad (2)$$

$F_{min}$: Minimum feature value
$F_{max}$: Maximum feature value

8. After the pre-processing stages, in the noise discrimination stage (stage 8), a 3-way or higher classifier function is applied to one or more selected normalized features for the segment of the ECG signal to classify the original segment of ECG signal into one of at least three classes. The HR of the segment may also be used in the process of classifying the segment. For convenience, the invention will be described with reference to an embodiment that uses a three-way classifier, but as noted above the invention is not limited to this. In this embodiment using a three-way classifier, the original ECG signal is classified into one of the following 3 classes: noise, abnormal sinus rhythm (for example Atrial Fibrillation), and Normal Sinus Rhythm.

9. If the segment is classified as either abnormal sinus rhythm or Normal Sinus Rhythm, the heart rate, for example the heart rate as determined at stage 1a, is returned as stage 9. If this heart rate is outside the normal physiological bounds, a notification will be triggered.

10. Otherwise, the segment of ECG signal is classed as having a high noise level, and an invalid code is returned at stage 10.

FIG. 1 further shows one possible way in which the three-way classification stage (stage 8) could be implemented. In this implementation, stage 8 initially includes a determination (stage 8a) of whether the normalised features output from stage 7 indicate that the patient suffers from abnormal sinus rhythm (for example atrial fibrillation). If this determination is positive, the heart rate is output (stage 9a). If this determination is negative, stage 8 then includes a determination (stage 8b) of whether the normalised features output from stage 7 indicate excessive noise in the input ECG—and if this determination is positive an error code is output (stage 10), whereas if this determination is negative the heart rate is output (stage 9b).

The classification of a segment of the ECG signal at stage 8 may be carried out by using two (or in principle more than two) of the normalised features determined for the segment at stage 7 or by using the HR and one (or in principle more than one) of the normalised features determined for the segment. Two features, HR and RMSSD as an example, may be considered as a 2-D feature space (that is with HR along one axis and RMSSD along the other axis). In this space, three different clusters corresponding to noise, normal sinus rhythm, and abnormal sinus rhythm can be observed. By partitioning up this feature space, and allocating different regions of the partitioned space to pre-determined classes such as noise, normal sinus rhythm and abnormal sinus rhythm, a segment of ECG signal may be classified based on the feature values for the segment alone.

Figure 5:
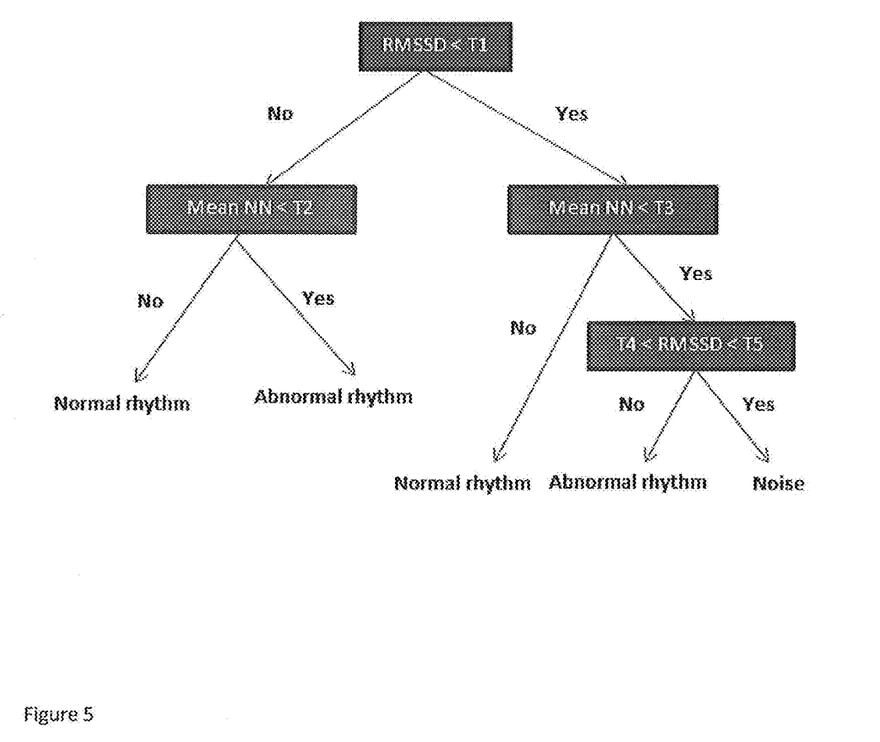
FIG. 5 shows an example of a decision tree suitable for use in an embodiment of the invention.

FIG. 5 shows a further example of how a segment may be classified into one of noise, normal sinus rhythm and abnormal sinus rhythm using two of the normalised features obtained for the segment. In the example of FIG. 5 the two features are the mean NN interval for the segment and the RMSSD for the segment. FIG. 5 illustrates the use of a "decision tree" to classify a segment of ECG signal based on its mean NN interval and RMSSD. There are several types of classifiers that can be used to classify a segment of ECG signal but a decision tree technique may be advantageous because it can give the best performance to computational requirements ratio. In principle, a decision tree starts at the highest level (or the root node of the tree), where it compares a pre-computed feature with a threshold value T1, in determining which branch of the tree to take. It then makes further comparisons at other nodes of the tree until it arrives at the leaf of the tree, where the class is determined.

In the example of FIG. 5, the decision tree starts by comparing the normalised RMSSD value for the segment with the threshold value T1. Depending on the result of this comparison, the mean NN value of the segment is then compared with a threshold T3 (if the normalised RMSSD value for the segment is less than T1) or the mean NN value of the segment is then compared with a threshold T2 (if the normalised RMSSD value for the segment is greater than T1). In the example of FIG. 5 the result of this second comparison may be sufficient to classify the segment, although in the case of RMSSD<T1 and Mean NN<T3 a further comparison is performed.

Where a decision tree is used, the tree may for example be created using an induction algorithm which minimises the classification error by selecting the best feature and the best threshold(s) for the comparison at each node of the tree.

While the above examples of classifying a segment of the ECG signal use two features (eg. HR and RMSSD; or mean NN value and RMSSD), in principle, the invention is not limited to this and the classification may, for example, make use of only one feature, or may make use of more than two features.

In the example of FIG. 5 the decision tree classifies a segment of ECG signal into one of three classes, namely noise, abnormal sinus rhythm and normal sinus rhythm. The invention is not however limited to this as already noted, and the invention may classify an ECG segment into one of four, or even more, classes—for example into the four classes of noise, first abnormal sinus rhythm, second abnormal sinus rhythm (different from the first abnormal sinus rhythm), and normal sinus rhythm. An embodiment in which an ECG segment is classified into one of four or more classes may again be implemented using a decision tree or other suitable classifier.

The present invention has at least the following advantages.

Firstly the proposed technique is more robust in terms of determining the level of confidence in the results of the HR algorithm, by making use of detection module, for example an arrhythmia detection module, to distinguish between noise, normal sinus rhythm, and abnormal or aperiodic sinus rhythm such as AF). This feature provides an efficient method for a low-cost wireless monitor to achieve a high level of accuracy in the computed heart rate, without discarding an excessive number of results.

Since the heart rate of subjects suffering from AF is likely to be high, this approach can allow earlier notifications to be sent as the corresponding heart rate is less likely to be rejected. Treatment can then be administered more quickly.

By taking a modular approach to the design of the confidence level computation module, the algorithm can be customized to different types of platforms by enabling/disabling different sub-modules, to exploit different trade-offs between confidence level accuracy and the resources (memory and execution speed) required for implementation.

Figure 3:
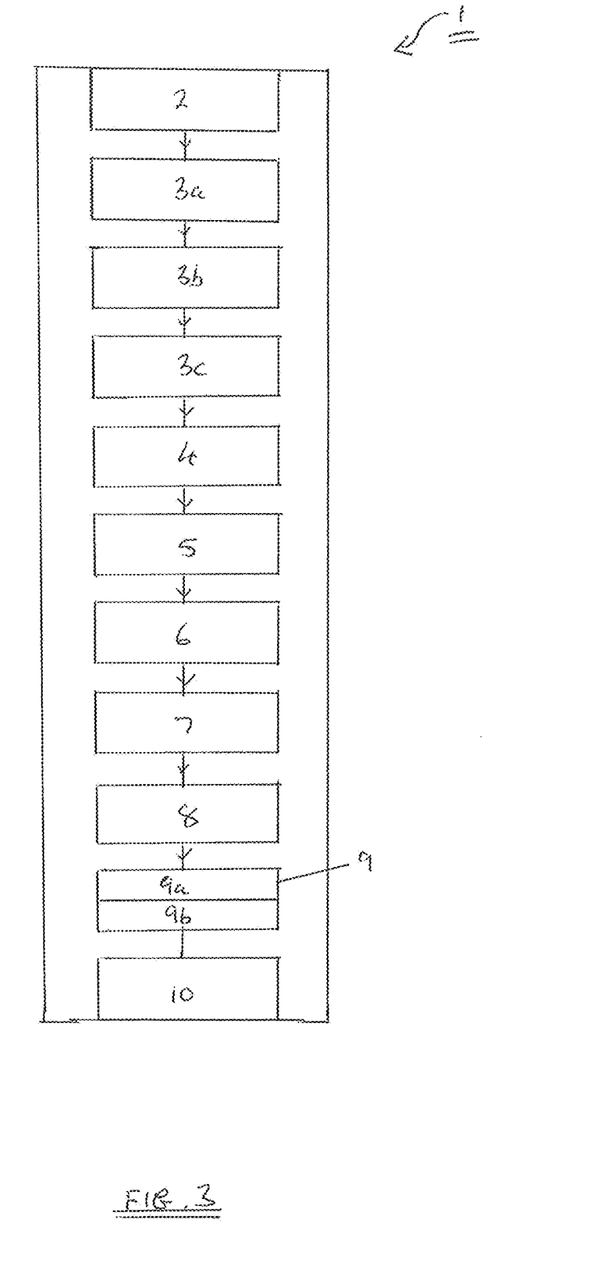
FIG. 3 illustrates principal features of a device according to the present invention.

FIG. 3 is a block diagram showing principal features of an apparatus according to the invention. The apparatus 1 has an input 2 for receiving segments, of a pre-determined length, of an ECG signal, for example in digitised form. Alternatively, the apparatus may receive a complete ECG signal, and comprise a segmenter (not shown in FIG. 3) for segmenting the received ECG signal into segments of a pre-determined length.

The apparatus has a module 3a for determining the patient's heart rate from a segment of the ECG signal, and this module 3a may for example be a QRS detection and HR determination. The apparatus also has a module 3b for determining the noise level in the segment of ECG signal, and a module 3c for determining a confidence level in the HR obtained from the segment of ECG signal.

The apparatus comprises a determination module 4, for determining whether the segment of ECG signal is valid or invalid (using the noise level determined for the segment), and outputting the determined HR if the segment of ECG signal is determined to be valid.

The apparatus comprises a detrending module 5 for detrending the set of RR intervals obtained using the QRS detection algorithm as described for stage 4, a filter module 6 for filtering the detrended set of RR intervals to produce a set of NNs as described for stage 5, a feature generating module 7 for determining features from the NNs as described for stage 6, and a normalising module 8 for normalising the features as described for stage 7.

The apparatus further comprises a 3-way classification module 9 for determining, from the normalised features obtained by the normalising module 8, whether the HR obtained from a segment is indicative of an abnormal or aperiodic sinus rhythm (such as AF), a normal heart beat, or is invalid owing to excessive noise, and an output module 10 for outputting either the determined HR or an indication that the determined HR is invalid. In one embodiment, the 3-way classification module 9 comprises a module 9a for determining whether the HR obtained from a segment is indicative of an abnormal or aperiodic sinus rhythm, and a module 9b for determining whether the HR obtained from a segment of the ECG signal is invalid owing to excessive noise in the ECG signal.

It should be understood that the apparatus of FIG. 3 may be implemented in many ways. In particular one or more of the described modules may be implemented in software, and indeed modules 2 to 10 may be implemented by a suitably programmed processor.

Figure 4:
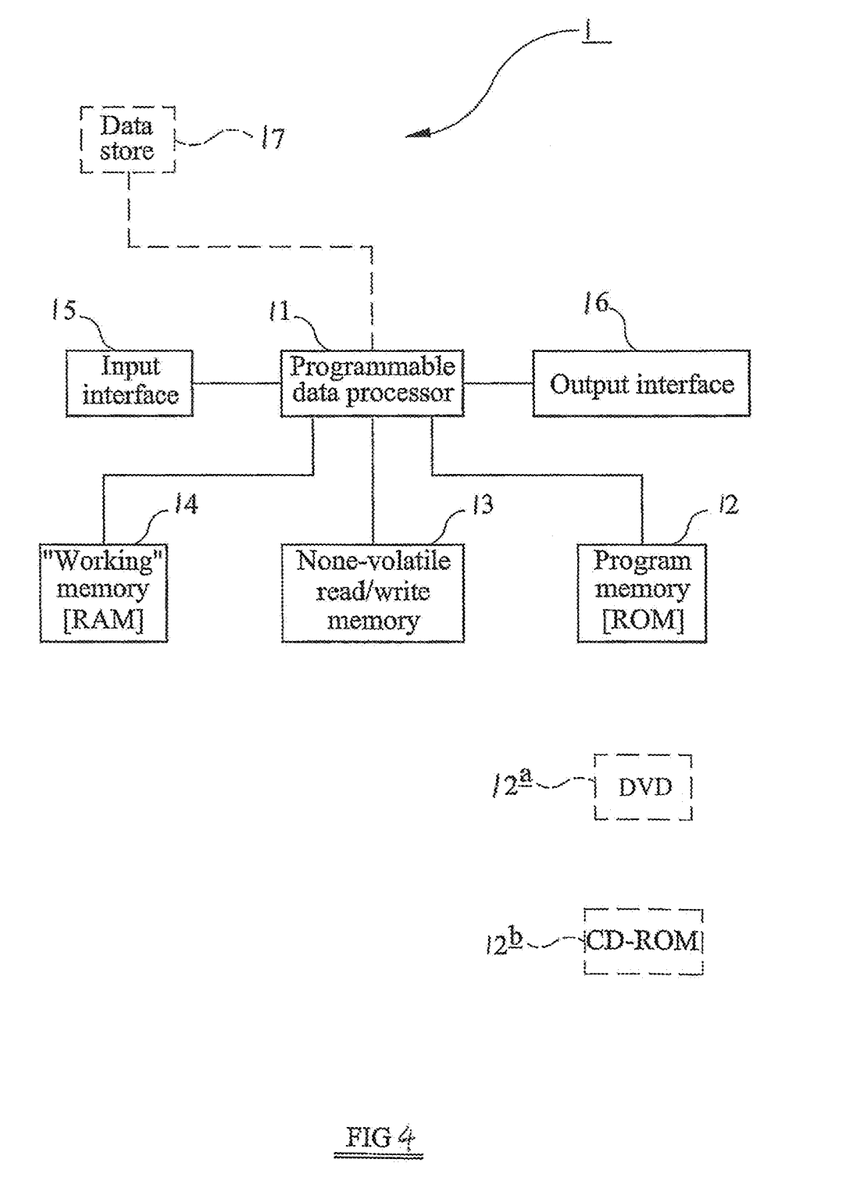
FIG. 4 is a schematic block diagram of an apparatus for performing a method according to the present invention.

FIG. 4 is a schematic block diagram of an apparatus 18 that is able to perform a method according to the present invention.

The apparatus 18 comprises a programmable data processor 11 with a program memory 12, for instance in the form of a read only memory (ROM), storing a program for controlling the data processor 11 to process an ECG signal, for example a single lead ECG signal, by a method of the invention. The apparatus further comprises non-volatile read/write memory 13 for storing, for example, any data which must be retained in the absence of a power supply. A "working" or "scratch pad" memory for the data processor is provided by a random access memory RAM 14. An input device 15 is provided, for instance for receiving user commands. One or more output devices 16 are provided, for instance, for displaying information relating to the progress and result of the processing. The output device(s) may be, for example, a printer, a visual display unit, or an output memory.

The ECG signal may be supplied via the input device 15 or may optionally be provided by a machine-readable data store 17.

The results of processing the ECG signal (that is, the determined heart rate or an indication that the ECG segment is invalid) may be output via the output device 16, may be stored, or may be transmitted to a user as, for example an SMS message or an e-mail.

The program for operating the system and for performing the method described hereinbefore is stored in the program memory 12, which may be embodied as a semiconductor memory, for instance of the well-known ROM type. However, the program may well be stored in any other suitable storage medium, such as a magnetic or optical data carrier, DVD 12a, CD-ROM 12b etc.

The invention claimed is:

1. A computer-implemented method comprising:
receiving an ECG signal from an ECG monitor;
determining, using a first determining module configured to determine a heart rate from a segment of an ECG signal, a first heart rate from a first segment of said ECG signal received from said ECG monitor, the first segment having a pre-determined length, and determining, using a first determining module configured to determine a confidence level in a determined heart rate, a first confidence level in the determined first heart rate;
determining that the first confidence level does not exceed a predetermined value,
determining, using a determining module configured to determine a set of features from a segment of an ECG signal, a set of features from the first segment of the ECG signal; and
classifying, using a classification module, the first segment of the ECG signal based on one or more features selected from the determined set of features and the first heart rate;
wherein the classification module is adapted to classify the first segment of ECG signal by classifying the first segment of ECG signal into any one of at least three classes: noise, an abnormal sinus rhythm, and a normal sinus rhythm;
determining, using a second determining module configured to determine a heart rate from a segment of an ECG signal, a second heart rate from a second segment of an ECG signal, the second segment having a pre-determined length, and determining, using a second determining module configured to determine a confidence level in a determined heart rate, a second confidence level in the determined second heart rate;
determining that the second confidence level exceeds the predetermined value and
outputting, using an output module configured to output a heart rate, the determined second heart rate without classifying the second segment of the ECG signal.

2. A method as claimed in claim 1 and comprising, if classifying, using the classification module, the first segment of the ECG signal comprises classifying the segment of the ECG signal as an abnormal sinus rhythm or a normal sinus rhythm, outputting, using the output module, the determined first heart rate after classifying the first segment of the ECG signal.

3. A method as claimed in claim 1 and, if classifying, using the classification module, the first segment of the ECG signal comprises classifying the first segment of the ECG signal as indicative of noise, further comprising outputting an error indication.

4. A method as claimed in claim 1 wherein determining, using the first determining module configured to determine a confidence level in a determined heart rate, the first confidence level comprises determining a noise level in the first segment of the ECG signal.

5. A method as claimed in claim 1 wherein determining, using the determining module configured to determine a set of features from a segment of an ECG signal, the set of features comprises processing the first segment and determining the set of features from the processed segment.

6. A method as claimed in claim 1 wherein classifying, using the classification module, the first segment of the ECG signal comprises classifying the first segment of the ECG signal based on two features selected from the determined set of features and the heart rate.

7. A method as claimed in claim 1 wherein the ECG signal is a single lead ECG signal.

8. A non-transitory computer-readable medium containing instructions that, when executed on a processor, cause the processor to carry out a method as defined in claim 1.

9. A method as claimed in claim 1 wherein the first determining module configured to determine a heart rate from a segment of an ECG signal and the second determining module configured to determine a heart rate from a segment of an ECG signal comprise a single module.

10. A method as claimed in claim 1 wherein the first determining module configured to determine a confidence level in a determined heart rate and the second determining module configured to determine a confidence level in a determined heart rate comprise a single module.

11. An apparatus comprising:
a module configured to determine a first heart rate from a first segment of an ECG signal, the first segment having a pre-determined length, and to determine a first confidence level in the determined first heart rate;
a module configured to, if the first confidence level does not exceed a predetermined value, determine a set of features from the first segment of the ECG signal;
a classifying module configured to, if the first confidence level does not exceed the predetermined value, classify the first segment of the ECG signal based on features selected from the determined set of features and the first heart rate,
wherein the classifying module is configured to classify the heart rate determined from the first segment of ECG signal into any one of at least three classes: noise, an abnormal sinus rhythm and a normal sinus rhythm;
a module configured to determine a second heart rate from a second segment of an ECG signal, the second segment having a pre-determined length, and to determine a second confidence level in the determined second heart rate;
a module configured to determine that the second confidence level exceeds the predetermined value; and
a module configured to, if the second confidence level exceeds the predetermined value, output the second heart rate without classifying the second segment of ECG signal.

12. An apparatus as claimed in claim 11 and configured to, if the classifying module classifies the first segment of the ECG signal as an abnormal sinus rhythm or a normal sinus rhythm, output the determined first heart rate.

13. An apparatus as claimed in claim 11 and configured to classify the first segment of the ECG signal based on two features selected from the determined set of features and the heart rate.

14. An apparatus as claimed in claim 11 and further comprising an input for receiving an ECG signal.

15. An apparatus as claimed in claim 14 and comprising a segmenter module configured to segment an ECG signal received at the input.

16. A system comprising an apparatus as defined in claim 14 and a single lead ECG system connectable to the input of the apparatus.

\* \* \* \* \*